(12) United States Patent
Kondo et al.

(10) Patent No.: US 9,329,125 B2
(45) Date of Patent: May 3, 2016

(54) PERFORATED-STRUCTURE BODY, MANUFACTURING METHOD THEREFOR, AND MEASUREMENT APPARATUS AND MEASUREMENT METHOD

(71) Applicant: Murata Manufacturing Co., Ltd., Nagaokakyo-shi, Kyoto-fu (JP)

(72) Inventors: Takashi Kondo, Nagaokakyo (JP); Seiji Kamba, Nagaokakyo (JP); Tetsuzo Hara, Nagaokakyo (JP); Masayuki Suzuki, Nagaokakyo (JP)

(73) Assignee: MURATA MANUFACTURING CO., LTD., Nagaokakyo-Shi, Kyoto-Fu (JP)

( * ) Notice: Subject to any disclaimer, the term of this patent is extended or adjusted under 35 U.S.C. 154(b) by 0 days.

(21) Appl. No.: 14/668,562

(22) Filed: Mar. 25, 2015

(65) Prior Publication Data

US 2015/0198527 A1    Jul. 16, 2015

Related U.S. Application Data

(63) Continuation of application No. PCT/JP2013/071637, filed on Aug. 9, 2013.

(30) Foreign Application Priority Data

Sep. 27, 2012    (JP) ................... 2012-214400

(51) Int. Cl.

| G01N 21/00 | (2006.01) |
| G01N 21/59 | (2006.01) |
| G01N 21/3581 | (2014.01) |
| G01N 21/01 | (2006.01) |
| G02B 5/18 | (2006.01) |
| H01J 37/20 | (2006.01) |
| G02B 21/34 | (2006.01) |
| G01N 21/03 | (2006.01) |

(52) U.S. Cl.
CPC ............ *G01N 21/59* (2013.01); *G01N 21/01* (2013.01); *G01N 21/3581* (2013.01); *G02B 5/18* (2013.01); *H01J 37/20* (2013.01); *G01N 2021/0339* (2013.01); *G01N 2201/02* (2013.01); *G01N 2201/061* (2013.01); *G02B 21/34* (2013.01); *Y10T 29/49* (2015.01)

(58) Field of Classification Search
CPC combination set(s) only.
See application file for complete search history.

(56) References Cited

U.S. PATENT DOCUMENTS

2008/0124521 A1*    5/2008    Niino ................... H01Q 17/004
                                                              428/138

FOREIGN PATENT DOCUMENTS

| JP | 2007-010366 A | 1/2007 |
| JP | 2010-236868 A | 10/2010 |
| WO | WO 2011/048992 A1 | 4/2011 |
| WO | WO 2011/070817 A1 | 8/2011 |

OTHER PUBLICATIONS

International Search Report for PCT/JP2013/071637, date of mailing Nov. 12, 2013.

* cited by examiner

*Primary Examiner* — Tri T Ton
(74) *Attorney, Agent, or Firm* — Arent Fox LLP

(57) ABSTRACT

A perforated-structure body having a plurality of apertures that penetrate from a first main surface to a second main surface of a perforated plate. Support substrates are stacked on at least one of the first main surface and the second main surface of the perforated plate so as to define a portion through which at least one of the apertures is exposed.

19 Claims, 15 Drawing Sheets

PERFORATED-STRUCTURE BODY, MANUFACTURING METHOD THEREFOR, AND MEASUREMENT APPARATUS AND MEASUREMENT METHOD

CROSS REFERENCE TO RELATED APPLICATIONS

The present application is a continuation of International application No. PCT/JP2013/071637, filed Aug. 9, 2013, which claims priority to Japanese Patent Application No. 2012-214400, filed Sep. 27, 2012, the entire contents of each of which are incorporated herein by reference.

FIELD OF THE INVENTION

The present invention relates to a perforated-structure body, and relates to a manufacturing method for the perforated-structure body, and to a measurement apparatus and a measurement method that employ the perforated-structure body.

BACKGROUND OF THE INVENTION

In the related art, a method in which electromagnetic waves are radiated in order to measure a characteristic of a measurement target material is known. An example of such a method is disclosed in the below-cited Patent Document 1. In Patent Document 1, a perforated-structure body is provided in which a large number of apertures are arranged. The perforated-structure body is irradiated with electromagnetic waves from a direction orthogonal to the apertures. Next, a measurement target material is arranged on the perforated-structure body and the perforated-structure body is irradiated with electromagnetic waves. A characteristic of the measurement target material is measured using the difference between the transmittance of the electromagnetic waves in the case where the measurement target material is not arranged on the perforated-structure body and the transmittance of the electromagnetic waves in the case where the measurement target material is arranged on the perforated-structure body. In Patent Document 1, it is described that for example the reflection of electromagnetic waves may be used instead of the transmittance of electromagnetic waves.

Patent Document 1: Japanese Unexamined Patent Application Publication No. 2007-10366

SUMMARY OF THE INVENTION

In the measurement method described in Patent Document 1, high measurement sensitivity can be achieved by making the size of the apertures in the perforated-structure body small and making the thickness of the perforated-structure body, that is, its dimension in the direction orthogonal to the apertures small.

However, the strength of the perforated-structure body is reduced when the thickness of the perforated-structure body is made smaller. As a result, the perforated-structure body is likely to bend when the measurement target material is subjected to measurement. In addition, there is also a problem in that the perforated-structure body is easily damaged when the perforated-structure body is washed before and after the measurement.

An object of the present invention is to provide a perforated-structure body that has high mechanical strength and is not likely to bend or be damaged when being handled, and to provide a manufacturing method for the perforated-structure body, and a measurement apparatus and a measurement method that employ the perforated-structure body.

A perforated-structure body of the present invention is used in measurement of a characteristic of a measurement target performed by radiating electromagnetic waves. The perforated-structure body according to the present invention includes a perforated plate and a support substrate. The perforated plate has a first main surface and a second main surface that opposes the first main surface. A plurality of apertures are provided so as to penetrate from the first main surface to the second main surface. The support substrate is stacked on at least one main surface among the first main surface and the second main surface of the perforated plate. The support substrate has an opening or a cut out portion through which at least one of the apertures is exposed.

In a certain specific aspect of the perforated-structure body according to the present invention, in a portion where the support substrate is provided, the apertures of the perforated plate are filled with a material that forms the support substrate or the perforated plate.

In another specific aspect of the perforated-structure body according to the present invention, the support substrate includes first and second support substrates and the first and second support substrates are arranged so that at least one aperture is interposed therebetween.

In yet another specific aspect of the perforated-structure body according to the present invention, the first support substrate and the second support substrate are provided so as to intersect each other.

In another specific aspect of the perforated-structure body according to the present invention, a plurality of each of the first support substrate and the second support substrate are provided, the plurality of first support substrates and the plurality of second support substrates intersecting each other so as to have an opening that at least one of the apertures faces. It is preferable that the plurality of first support substrates and the plurality of second support substrates orthogonally intersect each other and that as a result a rectangular opening is formed.

In another specific aspect of the perforated-structure body according to the present invention, the first support substrate and the second support substrate diagonally intersect each other.

In yet another specific aspect of the perforated-structure body according to the present invention, a corner of a portion where the first support substrate and the second support substrate intersect each other has a curved shape.

In another specific aspect of the perforated-structure body according to the present invention, the second support substrate is provided so as to surround a periphery of the first support substrate. As examples of the shapes of the support substrates, the first perforated-structure body may have an annular shape and the second support substrate may have an annular shape having a larger inner dimension than the first support substrate.

In yet another specific aspect of the perforated-structure body according to the present invention, the support member has a central portion and first and second end portions that are arranged either side of the central portion, and a thickness of the first and second end portions is smaller than a thickness of the central portion.

In another specific aspect of the perforated-structure body according to the present invention, a sectional shape of the support member in a direction that connects the first and second end portions and in a thickness direction of the support member is an arch-like shape.

A manufacturing method for a perforated-structure body according to the present invention is a method for obtaining a perforated-structure body structured according to the present invention and includes the following steps.

A step of preparing the perforated plate having the plurality of apertures.

A step of forming the support substrate on at least one main surface of the perforated plate so that the support substrate has an opening or a cut out portion through which at least one of the apertures is exposed.

In a specific aspect of the manufacturing method for a perforated-structure body according to the present invention, the support substrate is formed using a plating method and the support substrate is formed such that part of the support substrate comes to be accommodated inside at least one of the apertures covered by the support substrate at the time of plating.

A measurement apparatus according to the present invention includes a perforated-structure body structured according to the present invention, an electromagnetic wave radiating apparatus that radiates electromagnetic waves onto the perforated-structure body, and an electromagnetic wave detection unit that measures a characteristic of electromagnetic waves that have been transmitted through the perforated-structure body. A measurement target is detected on the basis of a change in the characteristic of the electromagnetic waves caused by the existence of the measurement target which is arranged on the first or second main surface of the perforated-structure body or so as to be spaced apart from the first or second main surface of the perforated-structure body.

A measurement method according to the present invention includes a step of obtaining a reference value by radiating electromagnetic waves onto a perforated-structure body structured according to the present invention and detecting electromagnetic waves that have been transmitted through the perforated-structure body, a measurement step of arranging a measurement target on the first or second main surface of the perforated-structure body or so as to be spaced apart from the first or second main surface of the perforated-structure body, radiating electromagnetic waves and then detecting electromagnetic waves that have been transmitted through the perforated-structure body, and a detection step of detecting a characteristic of the measurement target on the basis of a difference between the electromagnetic waves obtained in the measurement step and the reference value of the electromagnetic waves obtained in the step of obtaining the reference value.

In the perforated-structure body according to the present invention, a support substrate is stacked on at least one main surface among a first main surface and a second main surface of a perforated plate and therefore the mechanical strength of the perforated-structure body can be effectively increased. Therefore, the perforated-structure body is not likely to bend or be damaged when being handled.

BRIEF DESCRIPTION OF THE DRAWINGS

FIG. 7(a) is a front view of the perforated-structure body and FIG. 7(b) is a schematic front view illustrating the first and second support members.

DETAILED DESCRIPTION OF THE PREFERRED EMBODIMENTS

Figure 1:
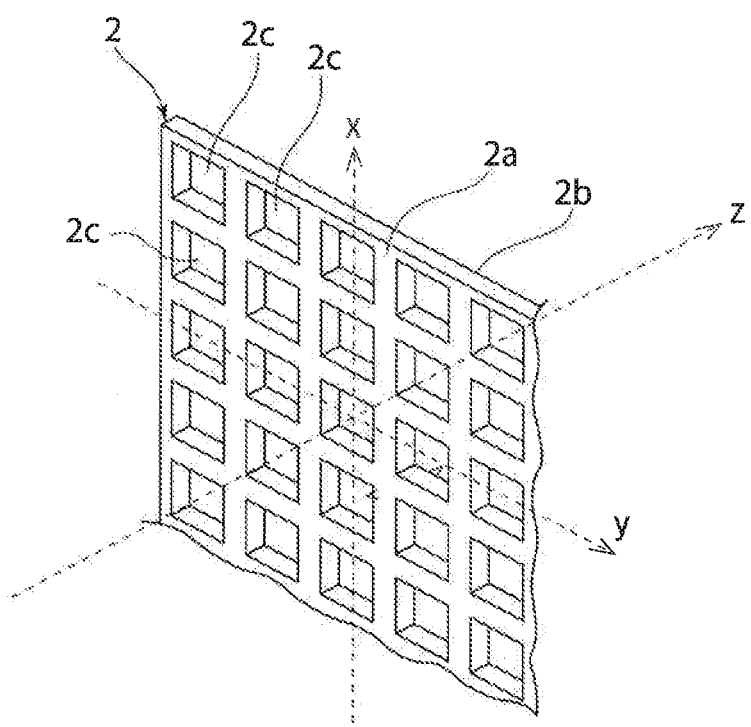
FIG. 1 is a schematic perspective view illustrating the exterior of a perforated plate of a perforated-structure body according to an embodiment of the present invention.

Hereafter, the present invention will be made clearer by describing specific embodiments of the present invention while referring to the drawings.

FIG. 1 is a schematic perspective view of a perforated plate used in a perforated-structure body according to a first embodiment of the present invention. A perforated plate 2 has a rectangular plate-like shape in this embodiment. A plurality of apertures 2c are arranged in a matrix pattern in the perforated plate 2.

The perforated plate 2 has a first main surface 2a and a second main surface 2b that is on the opposite side to the first main surface 2a. The plurality of apertures 2c penetrate through from the first main surface 2a to the second main surface 2b. In FIG. 1, a part of the perforated plate 2 in the vicinity of one corner portion of the perforated plate 2 is illustrated in an enlarged manner. In reality, the plurality of apertures 2c are provided in a greater number in the perforated plate 2. That is, the perforated plate 2 extends further toward portions indicated by cut lines from the portion illustrated in FIG. 1.

Figure 3A:
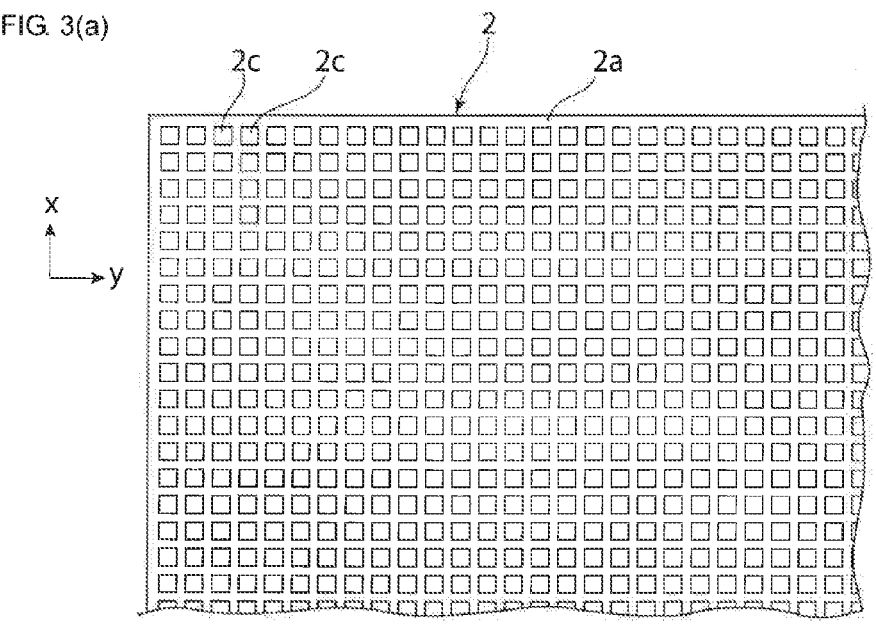
FIG. 3(a) is a front view of the perforated-structure body according to the embodiment of the present invention and FIG. 3(b) is a schematic front view illustrating first and second support members in the perforated-structure body according to the embodiment of the present invention.

An important part of the perforated plate 2 is illustrated as a front view in FIG. 3(a). This important part has the shape of the first main surface 2a side of the perforated plate 2 illustrated in FIG. 3(a) and forms part of the perforated plate 2 of this embodiment, and the perforated plate 2 of this embodiment extends in a direction opposite to an x direction and in a y direction in FIG. 3(a).

The apertures 2c have a square shape in this embodiment. The shape of the apertures 2c can of course be appropriately modified as will be described later.

The perforated plate 2 is preferably formed of a material having low resistance in this embodiment such as a metal or a semiconductor. It is further preferable that the material be a metal such as gold, silver, copper, iron, nickel or tungsten or an alloy of any of these metals.

Now, as indicated by x, y and z in FIG. 1, a vertical direction and a horizontal direction of the perforated plate 2 in FIG. 1 are an x-axis direction and a y-axis direction respectively, and a thickness direction of the perforated plate 2 is a z-axis direction.

Figure 2A:
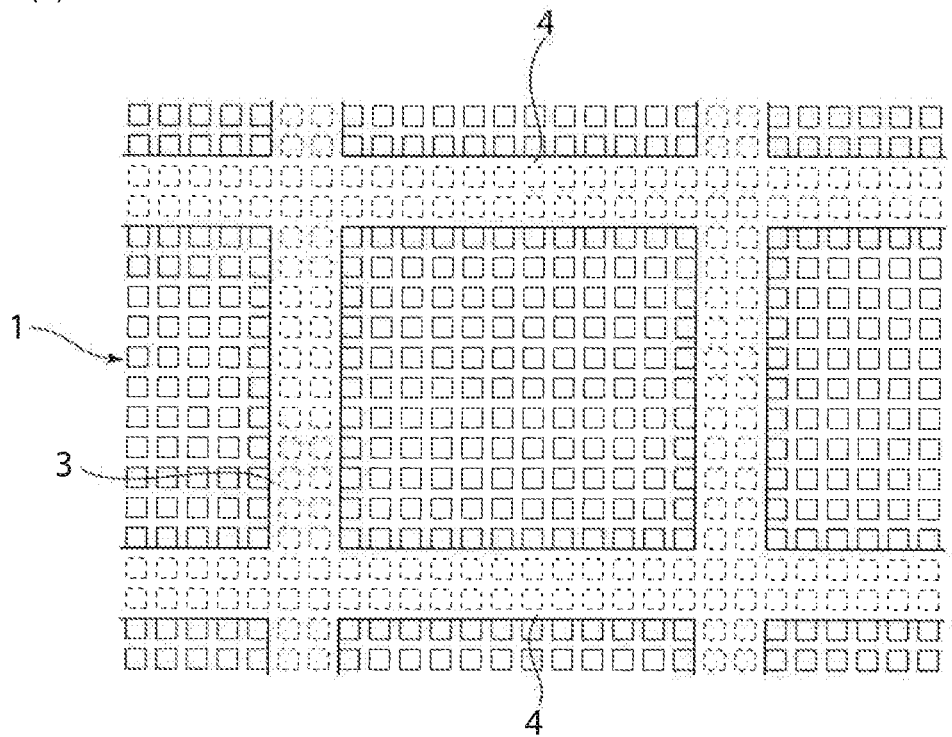
FIG. 2(a) is an enlarged front view illustrating an important part of the perforated-structure body according to the embodiment of the present invention and FIG. 2(b) is a sectional view illustrating in an enlarged manner part of the perforated-structure body of the embodiment.
Figure 2B:
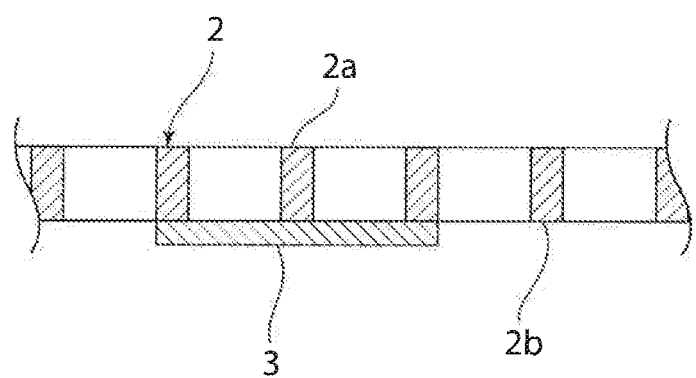

In addition, a feature of this embodiment is that a plurality of first support substrates 3 and a plurality of second support substrates 4, which are illustrated in FIG. 2(a), are stacked on the second main surface 2b of the perforated plate. A portion in which a first support substrate 3 is adhered is illustrated as a sectional view in an enlarged manner in FIG. 2(b).

Figure 3B:
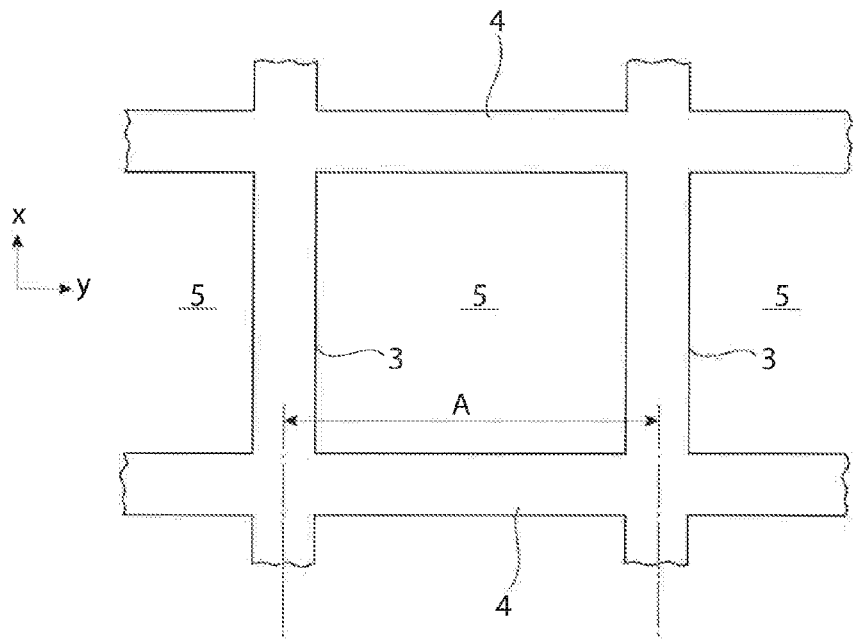

As illustrated in FIG. 3(a), when the perforated plate 2 is viewed from the first main surface 2a, that is, is viewed from the front, the apertures 2c are arranged in a matrix pattern as described above. As illustrated in FIG. 3(b), the plurality of first support substrates 3 extend in the x direction and the second support substrates 4 extend in the y direction.

In this embodiment, the plurality of first support substrates 3 and the plurality of support substrates 4 orthogonally intersect each other and are integrated with each other in the portions where they intersect. Therefore, as illustrated in FIG. 3(b), a square opening 5 is formed in a portion that is enclosed by a pair of first support substrates 3 extending parallel to each other and a pair of second support substrates 4 extending parallel to each other. In this embodiment, a plurality of square openings 5 are arranged in a matrix pattern, thereby forming a lattice-shaped support substrate portion.

In this embodiment, as described above, a configuration is adopted in which a support substrate includes the first support substrates 3 and the second support substrates 4, which are integrated with each other. Of course, in the present invention, so long as the support substrate includes an opening or a cut out portion that allows at least one of the apertures to be exposed therethrough, the shape of the support substrate is not particularly limited. For example, as in the case of a support substrate 31 illustrated in plan view in FIG. 10, the support substrate may be formed by performing punching on a sheet- or film-shaped member. That is, a plurality of openings 32 are formed by punching. In the case where the support substrate 31 is stacked on one main surface of the perforated plate 2, at least one aperture is exposed through one opening 32. That is, the openings 32 are provided so as to be each faced by at least one of the apertures.

The support substrate 31 having openings 32 can also be treated as a structure having the above-described first and second support substrates. That is, it is possible to think that portions that are arranged on both sides of an opening 32 and extend parallel to each other are first support substrates 31a and another pair of support substrate portions that extend parallel to each other form second support substrates 31b.

Figure 10:
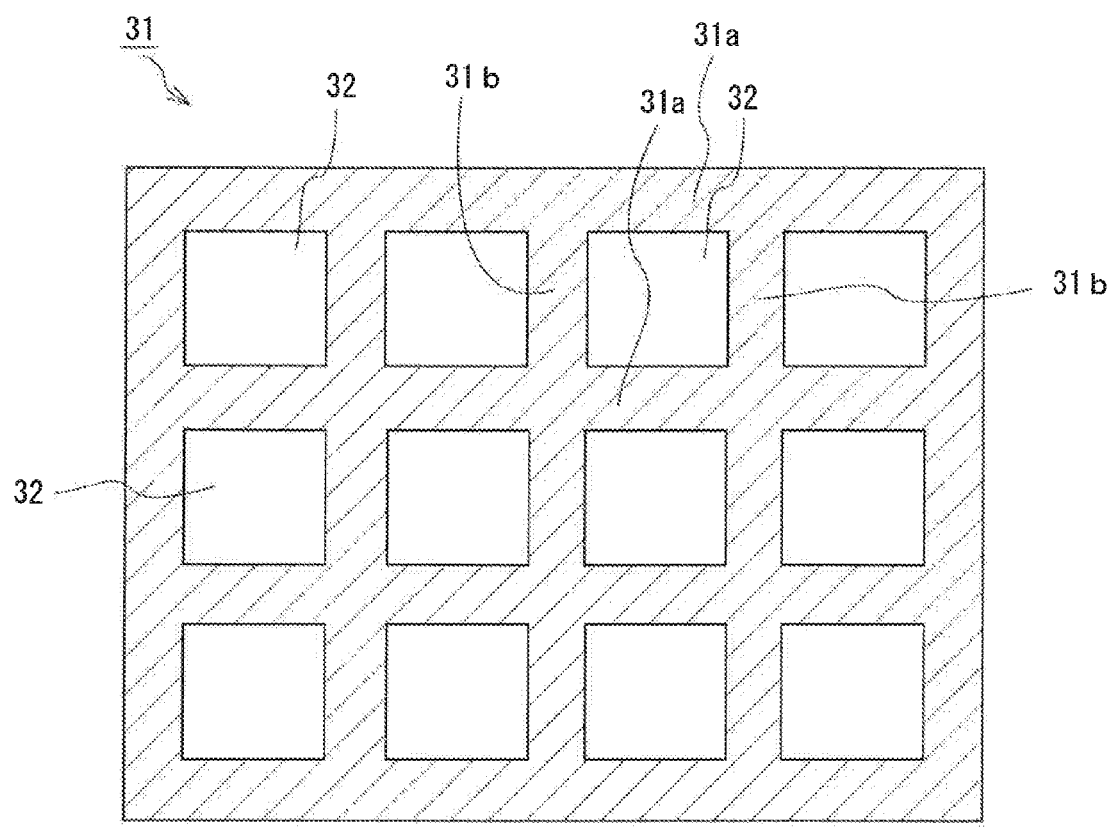
FIG. 10 is a plan view illustrating a first modification of support substrates.
Figure 11:
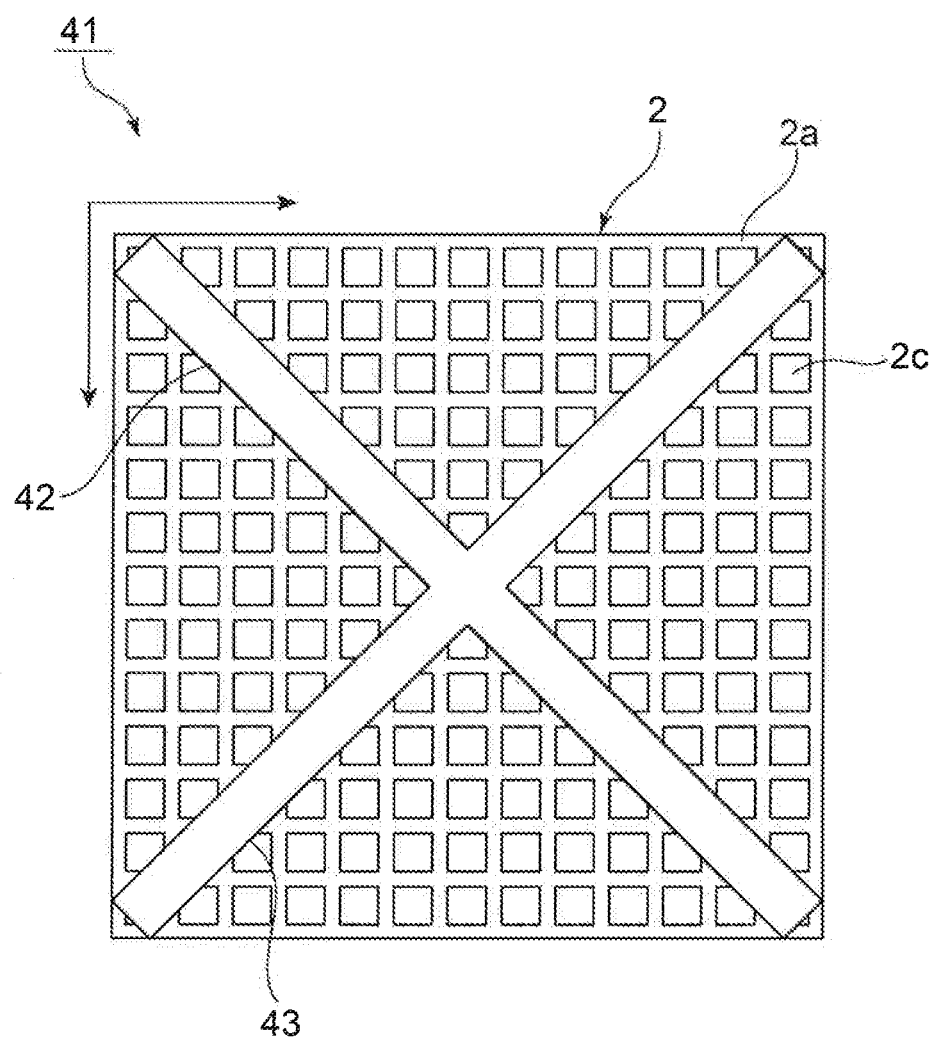
FIG. 11 is a front view illustrating a perforated-structure body equipped with support substrates according to a second modification.

In FIG. 10, the openings 32 are provided, but cut out portions that are open on one side may be provided instead of the openings 32.

The lattice-shaped support substrate portion is integrated by being adhered to the second main surface 2b of the above-described perforated plate 2. The adhesion can be achieved by for example using a method employing an adhesive or by forming the first and second support substrates by performing deposition on the second main surface 2b of the perforated plate 2.

Although the materials forming the first and second support substrates 3 and 4 are not particularly limited, a material having a low resistance is preferred such as a metal or a semiconductor. It is further preferable that the material be a metal such as gold, silver, copper, iron, nickel or tungsten or an alloy of any of these metals.

As has been described above, the first and second support substrates 3 and 4 are adhered to the second main surface 2b of the perforated plate 2. Therefore, as illustrated in FIG. 2(a), some of the apertures 2c among the plurality of apertures 2c provided in the perforated plate 2 are closed by the first support substrates 3 or the second support substrates 4. In this embodiment, the width-direction dimension of the first and second support substrates 3 and 4 is chosen such that two apertures 2c are arranged within each of the width direction of a first support substrate 3 and the width direction of a second support substrate 4. Of course, the width-direction dimension of the first and second support substrates 3 and 4 is not limited to this. Part of one of the apertures 2c may be closed by a first support substrate 3 and the remaining part may be arranged in an opening 5. That is, an edge of a first support substrate 3 may be provided at a position that divides a aperture 2c. The same applies to the second support substrates 4.

In addition, in this embodiment, a plurality of apertures 2c are located within each opening 5. In other words, a plurality of apertures 2c are located between the first support substrates 3 and the second support substrates 4. "Between the first support substrates 3 and the second support substrates 4", as illustrated in FIG. 2(a), also includes a mode in which the apertures 2c are arranged between two adjacent edges when a first support substrate 3 and a second support substrate 4 form orthogonal directions, that is, form two adjacent edges of a rectangle.

In the present invention, the configuration in which the apertures are arranged between the first support substrates and the second support substrates is not limited to a form in which the first support substrates and the second support substrates face each other and the apertures 2c are arranged between the first support substrates and the second support substrates, which face each other. That is, it is assumed that any form in which a plurality of apertures are arranged between the first support substrates and the second support substrates may be adopted.

In addition, in this embodiment, the first and second support substrates 3 and 4 are provided on the second main surface 2b side, but the first and second support substrates 3 and 4 may instead be provided on the first main surface 2a side. Furthermore, the support substrates 3 and 4 may be provided on both the first main surface 2a and the second main surface 2b.

In addition, the shape of the first and second support substrates 3 and 4 provided on the first main surface 2a and the shape of support substrates provided on the second main surface 2b side may be made different from each other.

The first and second support substrates 3 and 4 are composed of nickel in this embodiment. Of course, the first and second support substrates 3 and 4 are not limited to being composed of nickel, but a low resistance material is preferable and a metal or a semiconductor may be used. It is preferable that the material be a metal such as gold, silver, copper, iron, nickel or tungsten or an alloy of any of these metals. Whichever material is used, the perforated plate 2 can be reinforced by forming the first and second support substrates 3 and 4 using such a rigid material. Therefore, even if the thickness of a perforated-structure body 1 is made small, it is not likely to bend and further is not likely to be damaged when being handled such as when being washed.

Next, it will be illustrated that it is possible to perform detection on a measurement target material with high precision even when the first and second support substrates 3 and 4 are provided in the perforated-structure body 1 of this embodiment.

Figure 18:
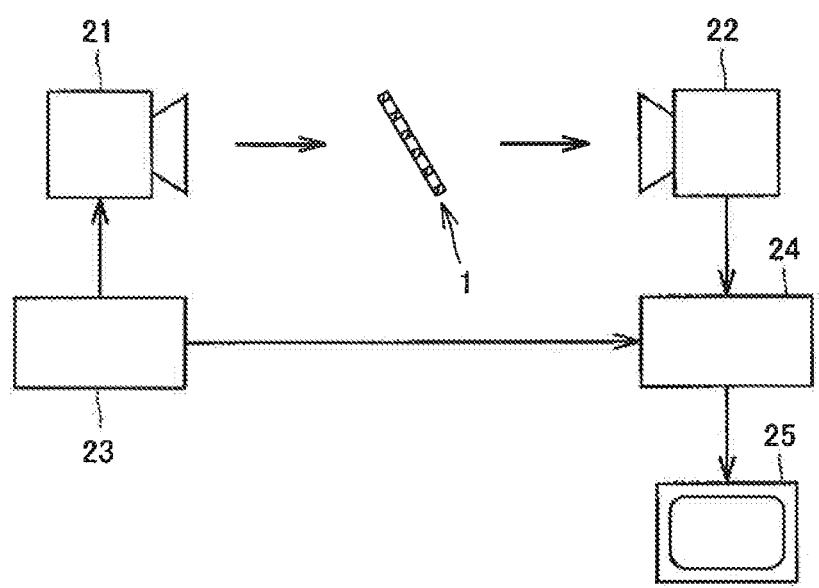
FIG. 18 is an outline structural diagram for describing a measurement apparatus that employs the perforated-structure body according to the embodiment of the present invention.

FIG. 18 is an outline structural diagram of a measurement apparatus in which the perforated-structure body of this embodiment is used.

This measurement apparatus includes a radiating unit 21 that radiates electromagnetic waves and a detection unit 22 that is for detecting electromagnetic waves that have been scattered by the perforated-structure body 1. In addition, the measurement apparatus further includes a radiation control unit 23 that controls operation of the radiating unit 21 and an analysis processing unit 24 that processes detection results of the detection unit 22. A display unit 25 that displays analysis results is connected to the analysis processing unit 24.

The term "scattering" used above refers to a broad concept including transmission, which is one form of forward scattering, and reflection, which is one form of backward scattering. It is preferable that the scattering be transmission or reflection. It is further preferable that the scattering be 0th-order-direction transmission or 0th-order-direction reflection.

In general, when d denotes the lattice spacing of a diffraction grating (spacing of apertures in this specification), i denotes the incidence angle, $\theta$ denotes the diffraction angle and $\lambda$ denotes the wavelength, the spectrum diffracted by the diffraction grating can be expressed by $d(\sin i - \sin \theta) = n\lambda$ ... Equation (1). 0th order in "0th-order direction" indicates a case where n in Equation (1) is 0. Since d and $\lambda$ cannot be 0, n=0 only in the case where $\sin i - \sin \theta = 0$. Therefore, "0th-order direction" means a direction obtained when the incidence angle and the diffraction angle are equal, that is, when the propagation direction of the electromagnetic waves does not change.

In a measurement method of this embodiment, electromagnetic waves are controlled by the radiation control unit 23 and radiated onto the perforated-structure body 1 from the radiating unit 21. The electromagnetic waves transmitted by the perforated-structure body 1 are detected by the detection unit 22. In the detection unit 22, the detected electromagnetic waves are converted into an electrical signal and supplied to the analysis processing unit 24. Then, the frequency characteristics of the transmittance are displayed on the display unit 25.

An example of the process of measuring a measurement target material using the perforated-structure body 1 will be described while referring to FIG. 4.

The following perforated-structure body was manufactured.

Dimensions of the perforated plate 2=circle with diameter of 6 mm×thickness of 1.2 μm. Material: Nickel Shape of apertures 2c: Square when viewed from front with dimensions of 1.8 μm×1.8 μm. Spacing between apertures 2c was 2.6 μm.

In addition, nickel was used as the material of the support substrates 3 and 4. Their width was 5.2 μm and their thickness was 5 μm. A lattice spacing A illustrated in FIG. 3(b), that is, the distance between the centers of the support substrates 3 and between the centers of the support substrates 4 was 108 μm. These support substrates were provided on the second main surface 2b side of the perforated plate 2.

An electromagnetic wave transmittance-frequency characteristic of the perforated-structure body 1 was measured by radiating an electromagnetic wave pulse including frequencies in the vicinity of 50 THz. As a result, results represented by the dotted line in FIG. 4 were obtained. Next, 2 μl of pure water was placed on the first main surface 2a of the perforated-structure body 1 as a measurement target material. The placed pure water filled the plurality of apertures 2c passed the first support substrates 3 and reached adjacent openings 5. In this way, an electromagnetic wave pulse including frequencies in the vicinity of 50 THz was radiated onto the perforated-structure body 1 to which the measurement target material had been attached and measurement was performed once more. As a result, results represented by the solid line in FIG. 4 were obtained.

Figure 4:
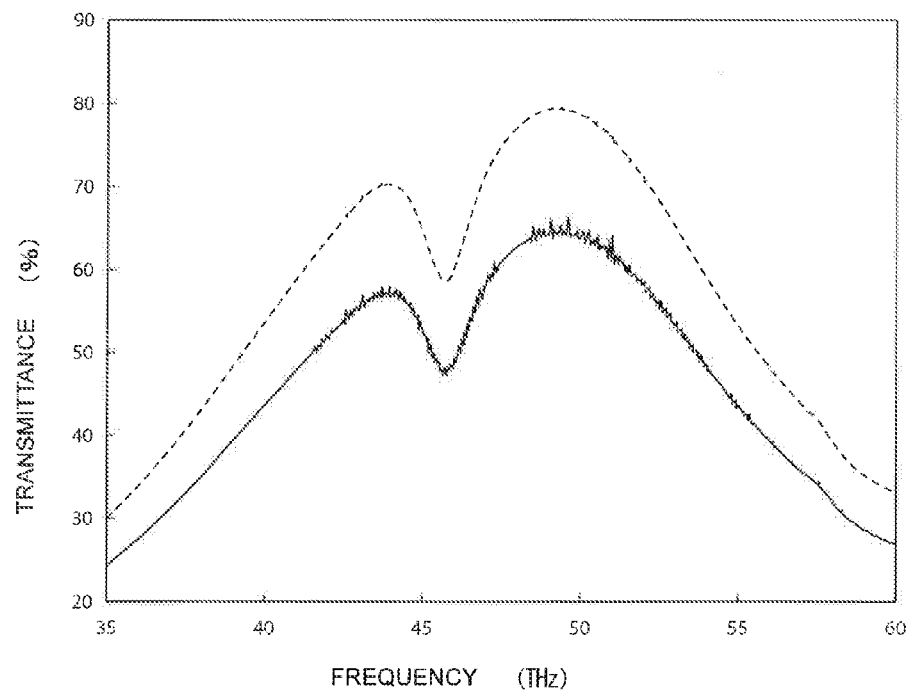
FIG. 4 illustrates the relationship between the transmittance of electromagnetic waves, which is measured using the perforated-structure body according to the embodiment of the present invention, and frequency, where the solid line represents the results in the case where there is no measurement target material and the dotted line represents the results in the case where there is a measurement target material.

Therefore, as is clear from FIG. 4, the transmittance is reduced when there is a measurement target material. Therefore, the amount, a physical property or so forth of the measurement target material can be detected on the basis of the ratio of the decrease of the transmittance at the peak value of the transmittance or the ratio of the decrease of the transmittance at another frequency position. Next, the following perforated-structure bodies of Examples 1 to 3, in which the first and second support substrates 3 and 4 are provided, and a perforated-structure body of a comparative example were prepared.

Example 1

Example 1 was a perforated-structure body with which the result represented by the solid line in FIG. 4 was obtained.

Example 2

Example 2 was the same as Example 1 except that the lattice spacing of the support substrates was changed to 180 μm.

Example 3

For Example 3, a perforated-structure body that was the same as that of Example 1 except that the lattice spacing of the support substrates was changed to 360 μm was prepared.

For the comparative example, the first and second support substrates were not provided in order to allow comparison and therefore the comparative example was formed of just the perforated plate.

Figure 5:
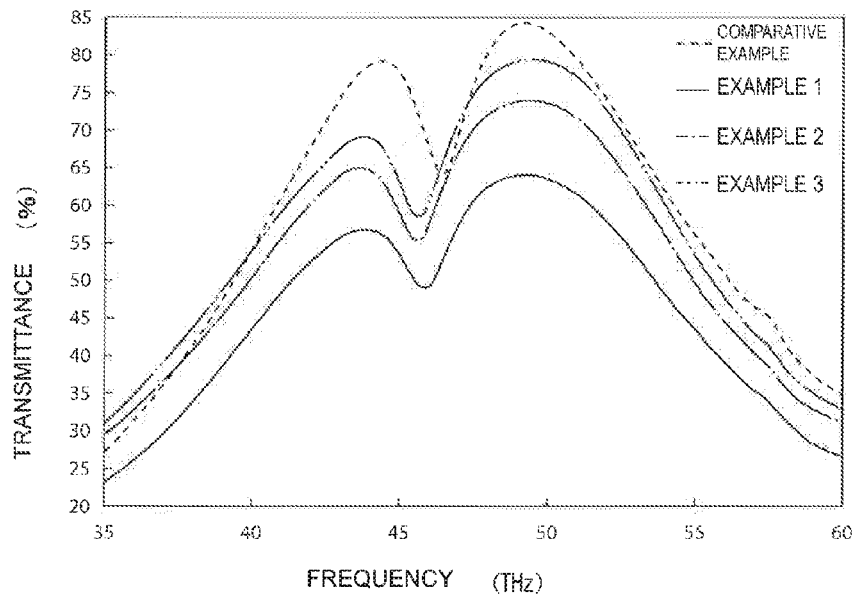
FIG. 5 illustrates the relationship between the transmittance of electromagnetic waves and frequency in the case where the perforated-structure body according to the embodiment of the present invention is used, where the dotted line represents the results in the case where a perforated-structure body of a comparative example that does not have first and second support members is used, and results for the case where the first and second support members having a lattice shape are provided are illustrated where the solid line represents the results in the case where the lattice spacing of the support members is 108 µm, the one-dot chain line represents the results in the case where the lattice spacing of the support members is 180 µm, and the two-dot chain line represents the results in the case where the lattice spacing of the support members is 360 µm.

The results for Examples 1 to 3 are represented by the solid line, the one-dot chain line and the two-dot chain line in FIG. 5. In addition, the result for the comparative example is represented by the dotted line in FIG. 5.

As is clear from FIG. 5, in the Examples 1 to 3 in which the support substrates 3 and 4 are provided, although the value of the transmittance is decreased compared with the comparative example, a transmittance-frequency characteristic having the same shape as in the comparative example is obtained. Therefore, in Examples 2 and 3, similarly to as in the case illustrated in FIG. 4, it is clear that when a measurement target material has been attached to the perforated-structure body 1, a characteristic of the measurement target can be detected on the basis of the ratio of the decrease of the transmittance or on the basis of the degree of shift of the frequency position of the peak transmittance.

The measurement target does not necessarily have to be attached to the first main surface or the second main surface of the perforated-structure body. In other words, the material to be subjected to detection may be arranged so as to be separated from the first main surface or the second main surface in the measurement apparatus and the measurement method of the present invention. The separation in this case is a separation of such a size that an electromagnetic field can be affected by the existence of the object to be measured when the measurement target is arranged so as to be separated from the surface. For example, when a sheet-shaped object, which causes an electromagnetic field to change, is arranged so as to be slightly separated from the perforated-structure body, as a measurement target, a characteristic of the sheet-shaped object can be measured with the present invention.

Next, it will be illustrated that the measurement target material can be analyzed with higher precision when the support substrates are provided compared to the case where the support substrates are not provided.

Example 4

The following perforated-structure body was manufactured.

Dimensions of perforated plate 2=diameter of 6 mm×thickness of 0.6 μm. Material; nickel Shape of apertures 2c; Square when viewed from front with dimensions of 1.8 μm×1.8 μm. Spacing between apertures 2c=2.6 μm.

In addition, nickel was used as the material of the support substrates 3. Their width was 5.2 μm and their thickness was 5 μm. The lattice spacing A illustrated in FIG. 3(b), that is, the distance between the centers of the support substrates 3 was 44.2 μm. These support substrates were provided on the second main surface 2b side of the perforated plate 2.

An electromagnetic wave transmittance-frequency characteristic of the perforated-structure body 1 was measured by radiating an electromagnetic wave pulse including a frequency of 50 THz. Next, as a measurement target, 10 μL of a protein water solution, whose concentration had been adjusted such that the deposited amount would be 20 ng or 40 ng per $mm^2$ of the perforated-structure body 1, was dropped onto the first main surface 2a of the perforated-structure body 1. An electromagnetic wave pulse including a frequency of 50 THz was radiated onto the perforated-structure body 1 to which the measurement target had been attached and measurement was performed once more.

An amount of shift of the frequency of the peak transmittance between before and after attachment of the measurement target was calculated. The calculated results are illustrated in Table 1 below.

Comparative Example 2

Other than the support substrates not being provided on the second main surface 2b side of the perforated plate 2, measurement and calculation were performed in the same way as in Example 4. The calculated results are illustrated in Table 1 below.

TABLE 1

| [ng/$mm^2$] | Comparative Example 2 Frequency Change Amount [Thz] | Example 4 Frequency Change Amount [Thz] |
| --- | --- | --- |
| 0 | 0 | 0 |
| 20 | 1.775 | 1.97 |
| 40 | 3.579 | 3.865 |

As illustrated in Table 1, in Example 4, it is clear that the amount of shift of the frequency of the peak transmittance is larger and the precision of analysis is increased compared with comparative example 2. This is thought to be because the support substrates were provided and therefore the amount of the measurement target dropped onto the perforated-structure body could be increased and consequently the measurement sensitivity was improved.

Figure 6:
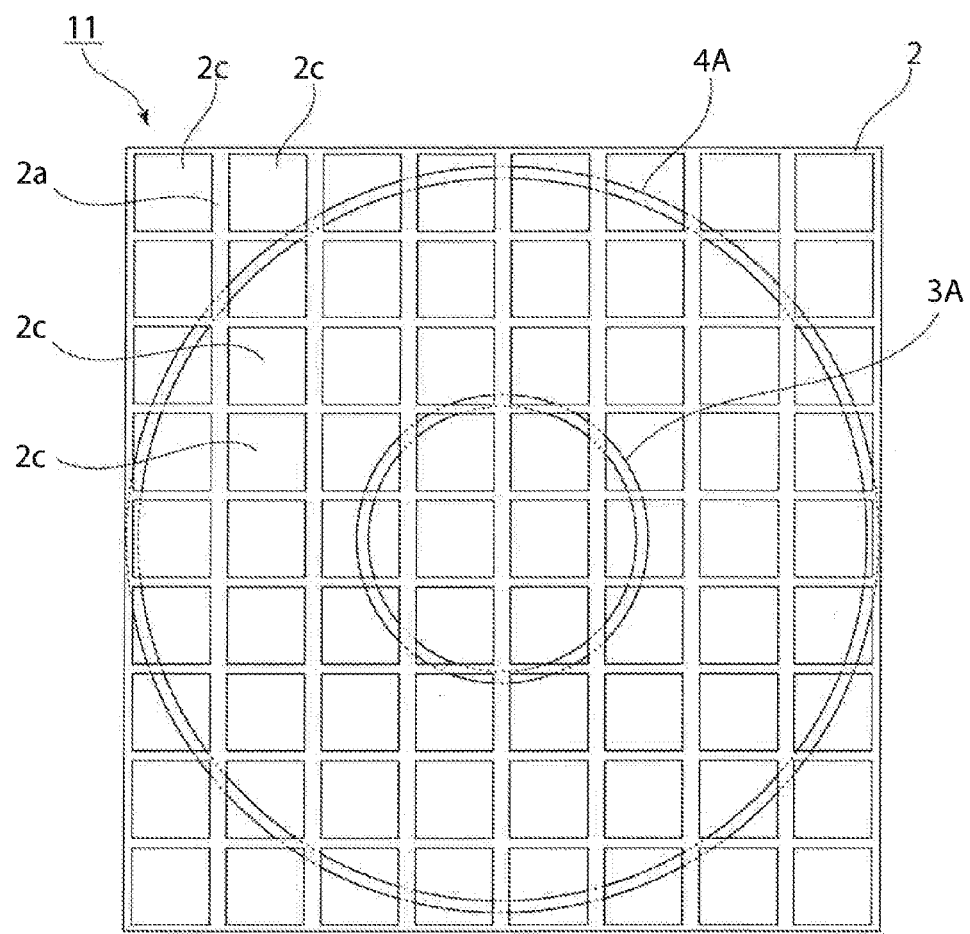
FIG. 6 is a schematic front view for describing a perforated-structure body according to another embodiment of the present invention.

In the above-described embodiment, a plurality of first support substrates 3 and a plurality of second support substrates 4 are orthogonal to each other and a plurality of square openings 5 are arranged in a matrix pattern. FIG. 6 is a schematic front view illustrating another embodiment of a perforated-structure body of the present invention. In a perforated-structure body 11 of this embodiment, the perforated plate 2 is the same as that of the first embodiment. The difference in this embodiment is that a first support substrate 3A and a second support substrate 4A have annular shapes.

That is, the first support substrate 3A has an annular, that is, a donut shape. The second support substrate 4A has an annular shape having a larger inner diameter than the first support substrate 3A. In other words, the second support substrate 4A is provided so as to surround the first support substrate 3A.

In this embodiment as well, a plurality of apertures 2c are provided between the first support substrate 3A and the second support substrate 4A. Therefore, similarly to as in the first embodiment, the perforated plate 2 can be reinforced by the first and second support substrates 3A and 4A. Therefore, the perforated-structure body 11 is not likely to bend or be damaged when being handled.

In FIG. 6, one or more third annular support substrates having different diameters may be added.

Figure 7A:
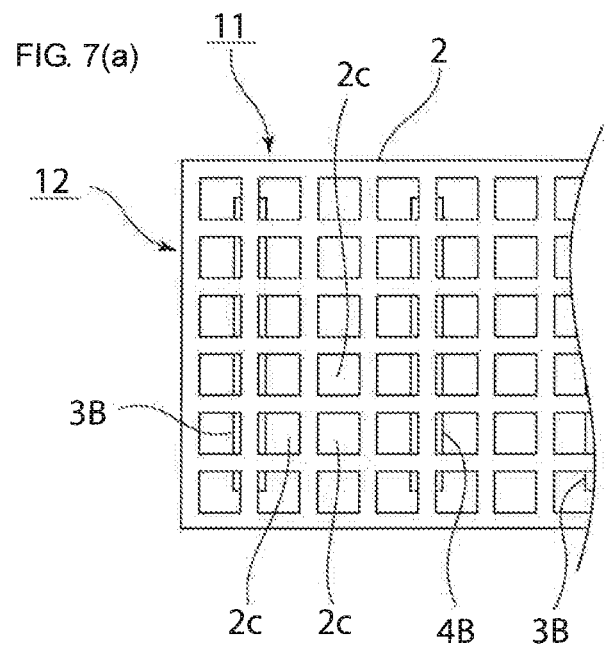
FIG. 7(a) and FIG. 7(b) are diagrams for describing a perforated-structure body according to yet another embodiment of the present invention, where
Figure 7B:
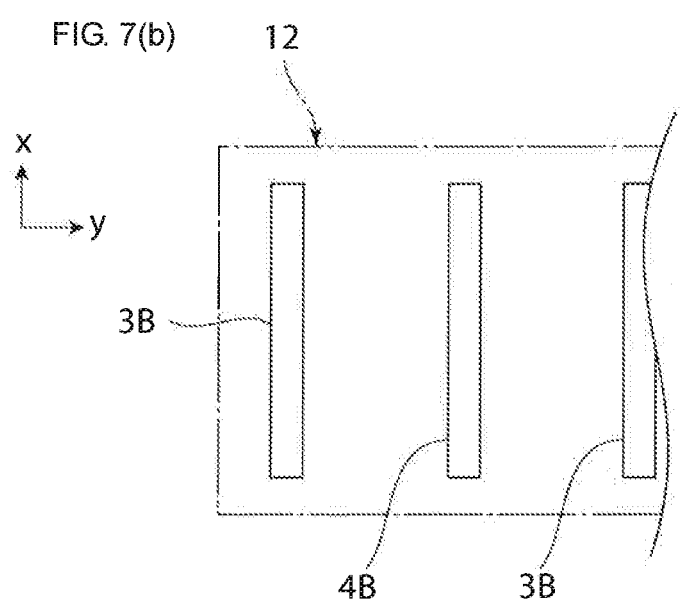

FIG. 7(a) and FIG. 7(b) are diagrams for describing a perforated-structure body according to yet another embodiment of the present invention, where FIG. 7(a) is a front view of the perforated-structure body and FIG. 7(b) is a schematic front view illustrating first and second support members 3 and 4 on the second main surface side with the perforated plate of the perforated-structure body being depicted in a see-through manner.

In a perforated-structure body 11 of this embodiment, a plurality of strip-shaped first support substrates 3B and a plurality of strip-shaped second support substrates 4B are alternately arranged on a second main surface of a perforated plate 12. The length direction of the strip-shaped first support substrates 3B and the strip-shaped second support substrates 4B is the x direction. The first support substrates 3B and the second support substrates 4B face each other in the y direction. Thus, the plurality of strip-shaped first and second support substrates 3B and 4B may be arranged so that there is at least one aperture 2c therebetween.

As described above, the shapes of the first and second support substrates in the present invention are not particularly limited and a loop-like shape such as an annular shape or a linear shape such as a strip shape may be adopted. In addition, any appropriate shape such as a rectangle, a triangle or a trapezoid can be adopted.

Referring to FIGS. 11 to 15, second to sixth modifications of the support substrates will be described. In a perforated-structure body 41 illustrated in FIG. 11, a first support substrate 42 and a second support substrate 43 are provided on the first main surface 2a of the perforated plate 2 so as to intersect each other. The first support substrate 42 has a band-like shape. The second support substrate 43 also has a band-like shape. In the portion where the first and second support substrates 42 and 43 intersect each other, the first and second support substrates 42 and 43 are integrated with each other. That is, the thickness of the intersection portion is the same as the thickness of the first and second support substrates 42 and 43.

Figure 12:
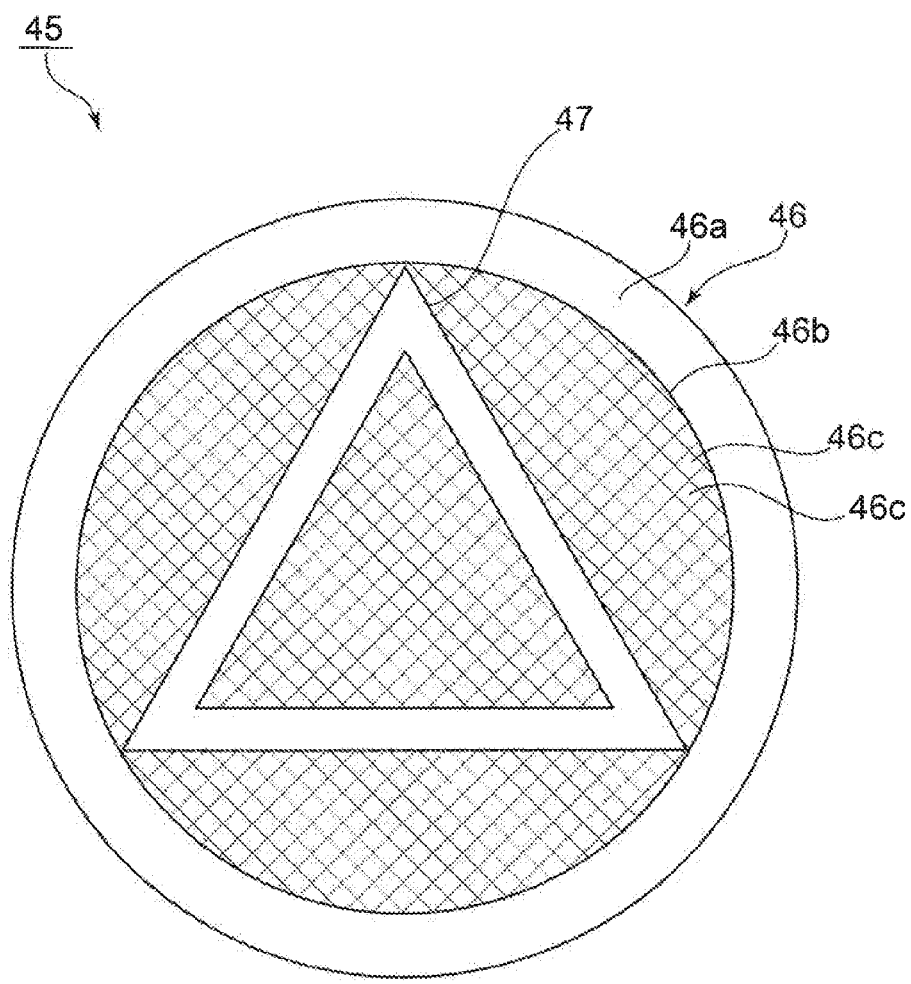
FIG. 12 is a schematic front view illustrating a perforated-structure body equipped with a support substrate according to a third modification.

In a perforated-structure body 45 illustrated in FIG. 12, a perforated plate 46 includes an annular-shaped outer circumferential portion 46a, a perforated portion 46b surrounded by the outer circumferential portion 46a and having a mesh-like shape and a great number of apertures 46c. A support substrate 47 has a triangular shape and is arranged on the perforated portion 46b.

Figure 13:
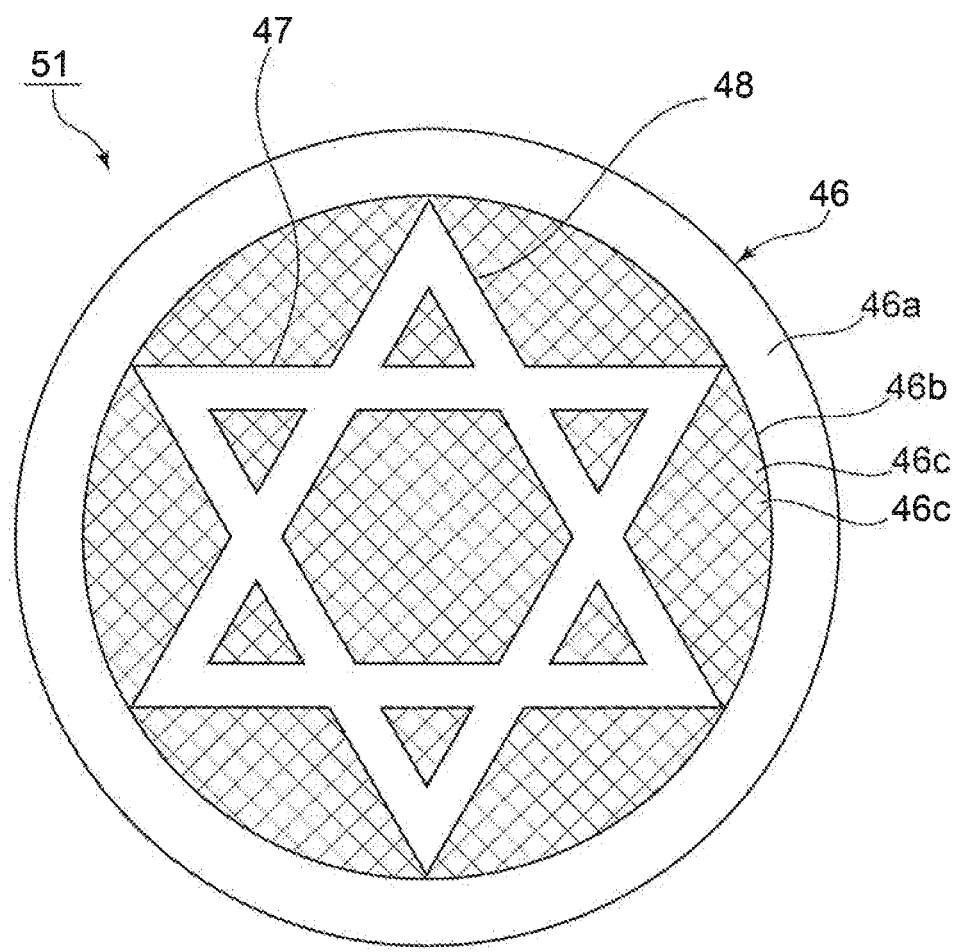
FIG. 13 is a schematic front view illustrating a perforated-structure body equipped with support substrates according to a fourth modification.

A perforated-structure body 51 illustrated in FIG. 13 also includes the perforated plate 46. A triangular-shaped first support substrate 47 and a triangular-shaped second support substrate 48 are stacked on the perforated portion 46b of the perforated plate 46. Here, intersection portions of the first and second support substrates 47 and 48 have the same thickness as the first and second support substrates 47 and 48, that is, the first and second support substrates 47 and 48 are not stacked on each other in the intersection portions but rather are continuous and integrated with each other.

Figure 14:
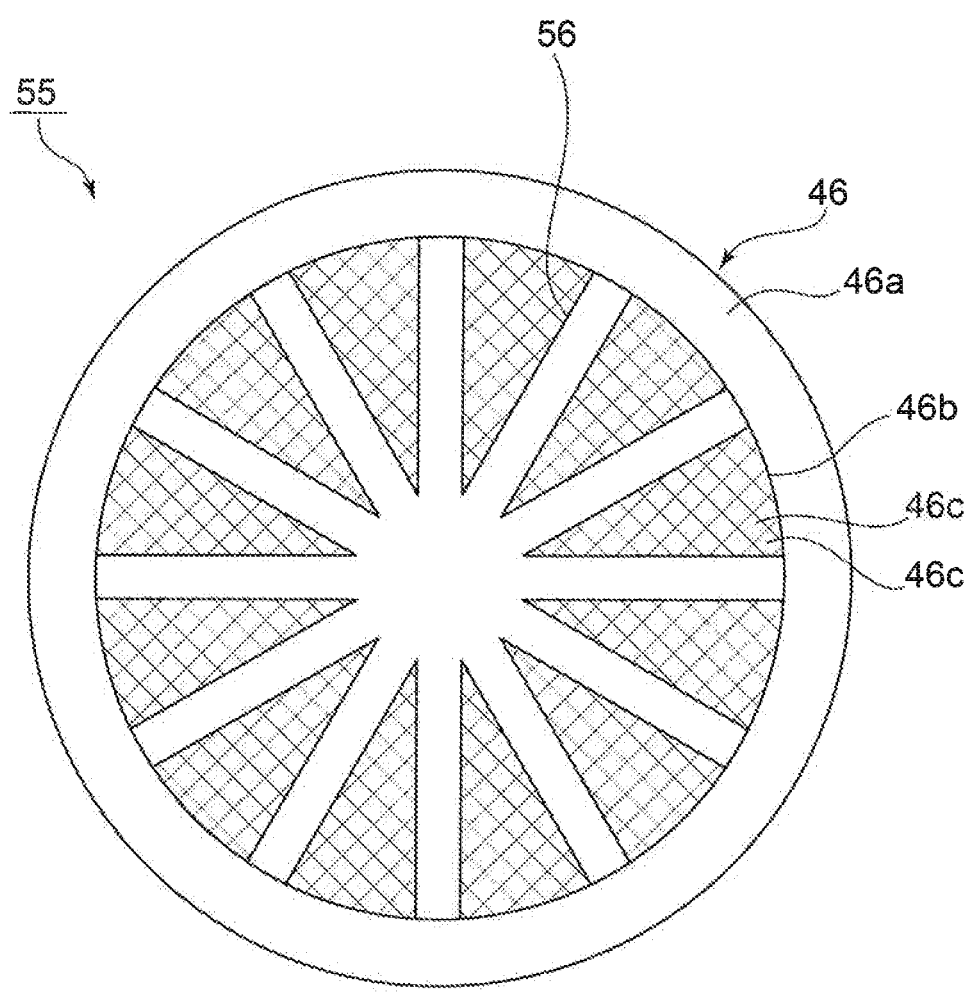
FIG. 14 is a schematic front view illustrating a perforated-structure body equipped with a support substrate according to a fifth modification.

In a perforated-structure body 55 illustrated in FIG. 14, a support substrate 56 having portions that extend radially from the center of the perforated portion 46b is stacked on the perforated portion 46b of the perforated plate 46.

The shape of a support substrate can be appropriately modified as in the second to fifth modifications illustrated in FIG. 11 to FIG. 14. In addition, a first support substrate and a second support substrate may have a portion where they intersect diagonally as in the case of the first support substrate 47 and the second support substrate 48 of FIG. 13 for example.

Figure 15:
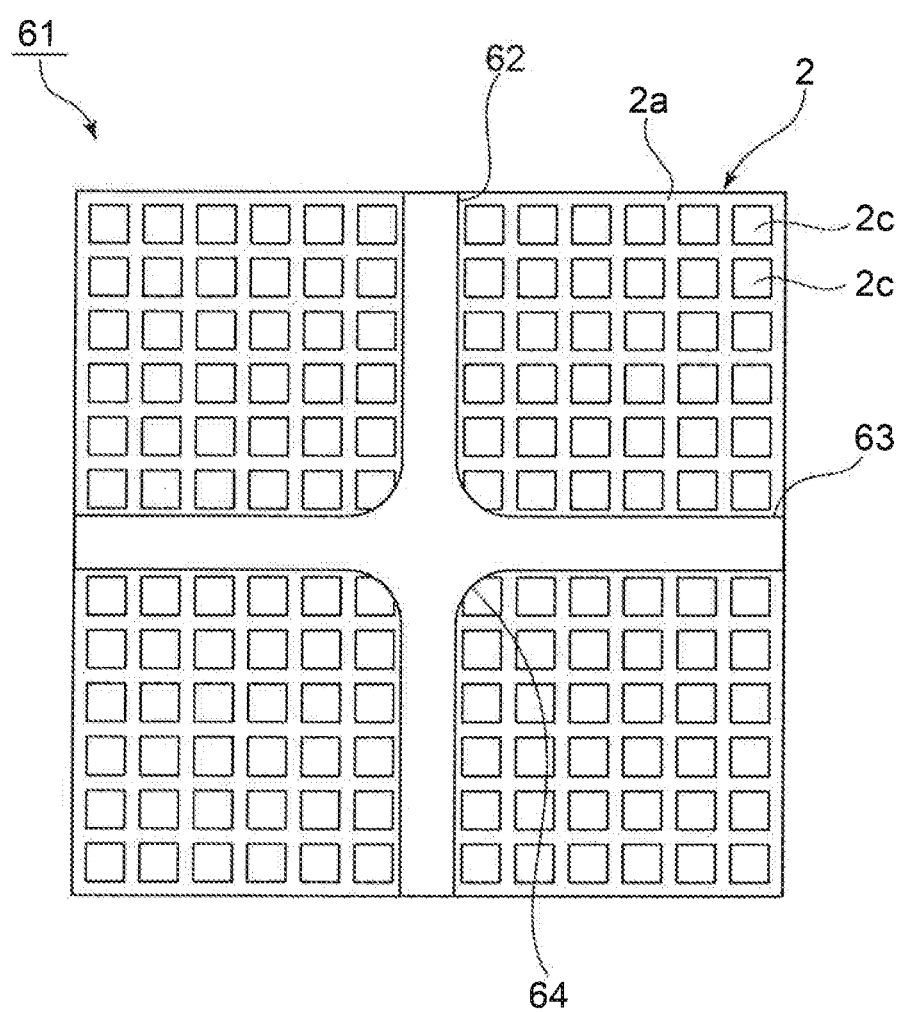
FIG. 15 is a schematic front view illustrating a perforated-structure body equipped with support substrates according to a sixth modification.

In a perforated-structure body 61 illustrated in FIG. 15, a first support substrate 62 and a second support substrate 63 are provided on the first main surface 2a of the perforated plate 2 so as to intersect each other in directions that are orthogonal to each other. Of course, the thickness of the intersection portion is the same as that of the first and second support substrates 62 and 63 in this intersection portion as well. That is, the first and second support substrates 62 and 63 are integrated with each other so as to form a substantially cross-like shape as illustrated in FIG. 15.

In this sixth modification, the outer circumferential edges of the corners where the support substrates intersect have a curved shape. That is, the corners of the portion where the first support substrate 62 and the second support substrate 63 intersect each other are rounded so as to include curved portions 64. The corners of the intersection portion may be rounded in this way. In this case, when forces are applied from both sides like when the intersection portion is being sandwiched, the applied forces can be more effectively dispersed. Therefore, the mechanical strength can be increased. Thus, the number of support substrates can be reduced while still obtaining the same mechanical strength. Alternatively, the thickness or the width of the support substrates can be reduced.

Figure 16:
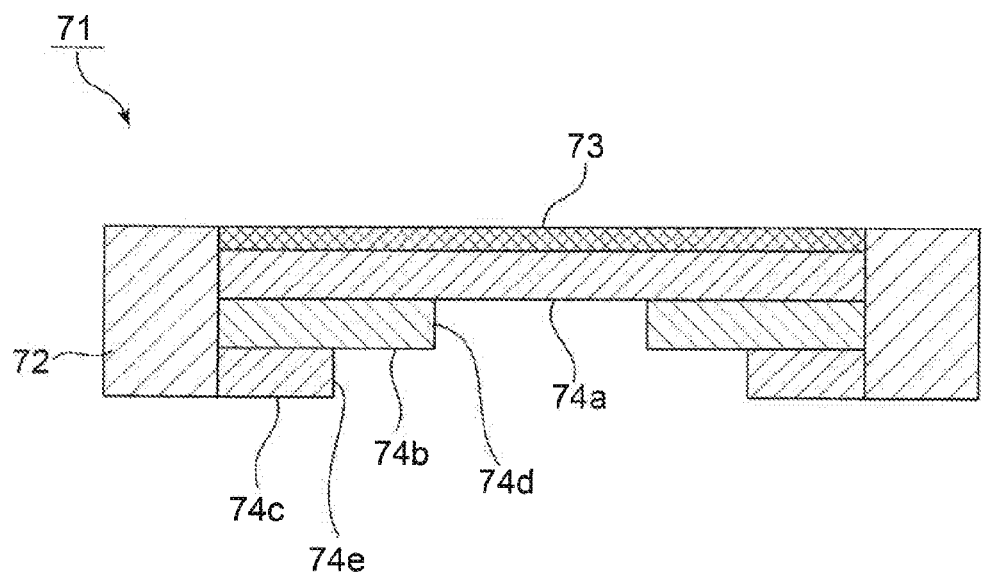
FIG. 16 is a schematic sectional view of a perforated-structure body equipped with support substrates according to a seventh modification.

FIG. 16 is a schematic sectional view illustrating a perforated-structure body equipped with support substrates according to a seventh modification. In a perforated-structure body 71, a perforated portion 73 is integrated with a support frame 72. A first support substrate 74a is stacked on one surface of the perforated portion 73. A second support substrate 74b is stacked on a lower surface of the first support substrate 74a and a third support substrate 74c is stacked on a lower surface of the second support substrate 74b. That is, the first to third support substrates 74a to 74c are stacked on one another, integrated and form a single support substrate.

The second support substrate 74b has an opening 74d. The third support substrate 74c has an opening 74e. The opening 74e is larger than the opening 74d. In addition, the centers of the openings 74d and 74e coincide with the center of the support substrate 74a.

Therefore, as illustrated in FIG. 16, in a section that passes through the center of the support substrate 74a and extends in a length direction of the support substrate 74a, the thickness of a central portion of a multilayer structure composed of the support substrates 74a to 74c is made thinner compared with the thickness of a first end portion of the multilayer structure at one end and a second end portion of the multilayer structure on the opposite side to the first end portion. In other words, in a sectional view, the multilayer structure is substantially arch-shaped. Thus, this arch-shaped structure is able to cause a force applied to the central portion thereof to be dispersed to first and second end portions thereof. Therefore, the mechanical strength can be increased. Therefore, the thickness or the width of the support substrates can be reduced while still obtaining the same mechanical strength. In addition, the number of support substrates can also be reduced.

Figure 17:
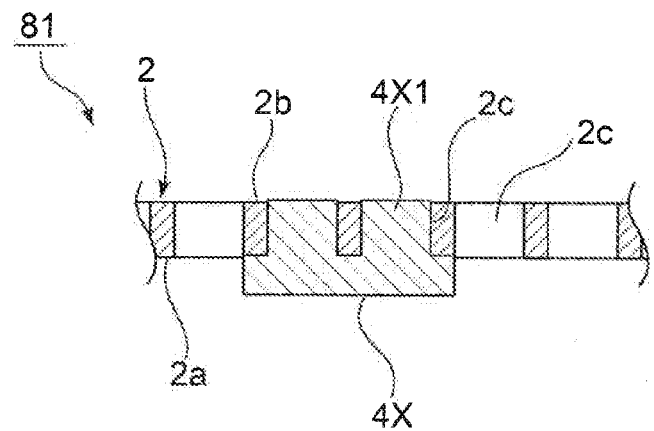
FIG. 17 is a partially cut away enlarged sectional view illustrating a modification in which part of a support substrate is accommodated inside apertures.

FIG. 17 is a partially cut away enlarged sectional view of a perforated-structure body for describing yet another modification of the support substrate.

In this modification, the same perforated plate 2 as in the first embodiment is prepared. The perforated plate 2 has the first main surface 2a and the second main surface 2b as described above. In this perforated-structure body 31, a support substrate 4X is stacked on the first main surface 2a. The support substrate 4X is composed of a metal and is deposited using a plating method. More specifically, the perforated plate 2 is arranged so that its first main surface 2a is on the upper side and the support substrate 4X is formed by a plating method. As a result, part of the support substrate 4X comes to be accommodated inside the apertures 2c. That is, filled portions 4X1, which are accommodated inside the apertures 2c, are provided. Consequently, the support substrate 4X is strongly adhered to the perforated plate 2. That is, the strength with which the support substrate 4X is adhered to the perforated plate 2 can be effectively increased by an anchor effect of the filled portions 4X1.

In addition, as yet another modification, a perforated plate may be prepared in which a region of the perforated plate on which a support substrate is to be formed is made flat by filling the apertures in advance. In this case, the support substrate should be formed on the perforated plate in the flat portion where apertures are filled. In other words, the apertures of the perforated plate may be filled with the material constituting the support substrate as illustrated in FIG. 17 or may be filled with the material forming the perforated plate.

The area of contact between the support substrate and the perforated plate can be increased similarly to as in the modification illustrated in FIG. 17 also in the case of the configuration in which the apertures are filled with the material that forms the perforated plate as described above. Therefore, the strength of adhesion can be increased. In the modification illustrated in FIG. 17, the strength of adhesion can be further increased by the anchor effect of the filled portions 4X1.

The support substrate 4X is not limited to being formed using a plating method as described above and may instead be formed using another deposition method such as vapor deposition or sputtering. The perforated plate 2 is preferably prepared as described above and then the support substrate 4X is preferably formed on one main surface of the perforated plate 2 using a plating method. Thus, a support substrate that is excellent in terms of adhesion strength can be formed.

Figure 8A:
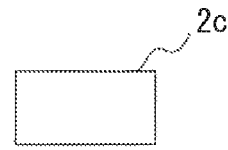
FIGS. 8(a) to 8(c) are front views illustrating modifications of the shape of apertures.
Figure 8B:
Figure 8C:
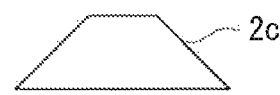
Figure 9:
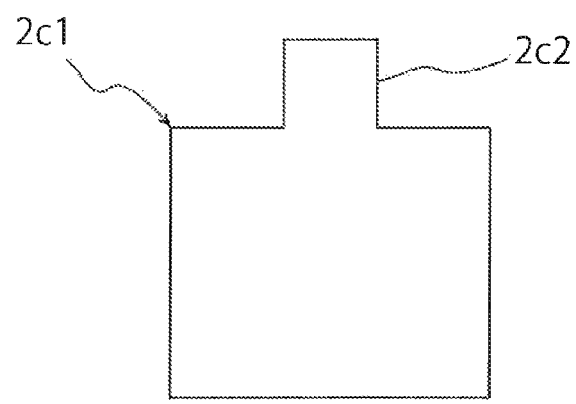
FIG. 9 is a front view illustrating yet another example of the shape of the apertures.

Furthermore, the shape of the apertures 2c is not limited to the square shape described in the embodiment and can be any appropriate shape such as the rectangular shape illustrated in FIG. 8(a), the circular shape illustrated in FIG. 8(b) or the isosceles trapezoid shape illustrated in FIG. 8(c). In addition, the shape is not limited to symmetrical shapes such as a square and a circle and may be a rectangle or a trapezoid. Moreover, the shape may be shape in which a smaller rectangular protrusion 2c2 is continuous with one edge of a rectangular aperture as in the case of the aperture 2c1 illustrated in FIG. 9.

It is sufficient that the plate-shaped perforated plate used in the present invention be a structure in which for example at least one aperture, which penetrates through the plate in a direction orthogonal to a main surface of the plate, is periodically arranged in at least one direction on the main surface of the plate. Here, all of the apertures may be arranged periodically or some of the apertures may be arranged periodically and the rest of the apertures may be arranged non-periodically so long as the effect of the present invention is not lost.

The perforated plate 2 is preferably a quasi-periodic structure or a periodic structure. A quasi-periodic structure is a structure that does not possess translational symmetry but in which an order is maintained in the arrangement of its constituent elements. Examples of a quasi-periodic structure include a Fibonacci structure, which is a one-dimensional quasi-periodic structure, and a Penrose structure, which is a two-dimensional quasi-periodic structure. A periodic structure is a structure that possesses spatial symmetry, a representative example of which being translational symmetry, and may be classified as a one-dimensional periodic structure, a two-dimensional periodic structure or a three-dimensional periodic structure in accordance with the number of dimensions of symmetry thereof. Examples of a one-dimensional periodic structure include a wire-grid structure and a one-dimensional diffraction grating. Examples of a two-dimensional periodic structure include a mesh filter and a two-dimensional diffraction grating. Among these periodic structures, a two-dimensional periodic structure is preferably used.

In addition, the dimensions of the apertures 2c in the perforated plate 2 should be appropriately set in accordance with the measurement method, the properties of the material of the plate-like perforated-structure body, the frequency of the electromagnetic waves to be used and so forth.

In addition, the average thickness of the perforated plate 2 is appropriately set in accordance with the measurement method, the properties of the material of the plate-like perforated-structure body, the frequency of the electromagnetic waves to be used and so forth and although it is difficult to give a general range for this thickness, in the case where forward scattered electromagnetic waves are to be detected, the thickness is preferably several times or less the wavelength of the electromagnetic waves to be used in the measurement. If the average thickness becomes larger than this range, detection of a signal may become difficult due to the intensity of the forward scattered electromagnetic waves becoming weaker.

All of the dimensions of the perforated-structure body 1 are not particularly restricted but they are to be decided upon in accordance with the area of a beam spot of the radiated electromagnetic waves.

The method for adhering the measurement target to the perforated-structure body 1 is not particularly limited. For example, a chemical bond between the surface of the perforated-structure body 1 and the measurement target may be caused to be formed. Alternatively, in the case where the measurement target possesses adhesiveness for example, the measurement target may be adhered to the perforated-structure body 1 by causing the measurement target to stick to the surface of the perforated-structure body 1 by utilizing this adhesiveness.

In addition, a host material, to which a measurement target is bonded in advance, may be adhered to the surface of the perforated-structure body 1. Examples of such a combination of a host material and a measurement target include antigen and an antibody, a carbohydrate chain and a protein, a lipid and a protein and a ligand and a protein.

It is preferable that at least part of the surface of the perforated plate 2 have conductivity. It is preferable that at least part of the surface be formed of a material that exhibits conductivity, that is, a conductor. The conductor is not particularly limited and an appropriate metal or semiconductor can be used.

REFERENCE SIGNS LIST

1 . . . perforated-structure body
2 . . . perforated plate
2a . . . first main surface
2b . . . second main surface
2c . . . aperture
2c1 . . . aperture
2c2 . . . protrusion
3, 4 . . . first, second support substrate
3A, 4A . . . first, second support substrate
3B, 4B . . . first, second support substrate
4X . . . support substrate
4X1 . . . filled portion
11 . . . perforated-structure body
12 . . . perforated plate
21 . . . radiating unit
22 . . . detection unit
23 . . . radiation control unit
24 . . . analysis processing unit
25 . . . display unit
31 . . . support substrate
31a . . . first support substrate
31b . . . second support substrate
32 . . . opening
41 . . . perforated-structure body
42, 43 . . . first, second support substrate
45 . . . perforated-structure body
46 . . . perforated plate
46a . . . outer circumferential portion 46b . . . perforated portion
46c . . . aperture
47, 48 . . . first, second support substrate
51 . . . perforated-structure body
55 . . . perforated-structure body
56 . . . support substrate
61 . . . perforated-structure body
62, 63 . . . first, second support substrate
64 . . . curved portion
71 . . . perforated-structure body
72 . . . support frame
73 . . . perforated portion
74a to 74c . . . first to third support substrate
74d, 74e . . . opening
81 . . . perforated-structure body

The invention claimed is:

1. A perforated-structure body comprising:
a plate having a first main surface and a second main surface that opposes the first main surface, and a plurality of apertures that penetrate from the first main surface to the second main surface; and
a support substrate that is stacked on at least one of the first main surface and the second main surface of the perforated plate, the support substrate defining a portion through which at least a first aperture of the plurality of apertures is exposed and at least a second aperture of the plurality of apertures is closed.

2. The perforated-structure body according to claim 1, wherein in a location where the support substrate is stacked on the at least one of the first main surface and the second main surface, the apertures of the plate are filled with a same material of the support substrate or the plate.

3. The perforated-structure body according to claim 1, wherein the support substrate includes first and second support substrates that are arranged so that at least one of the plurality of apertures is interposed therebetween.

4. The perforated-structure body according to claim 3, wherein the first support substrate and the second support substrate intersect each other.

5. The perforated-structure body according to claim 4, wherein a plurality of each of the first support substrate and the second support substrate are provided, the plurality of first support substrates and the plurality of second support substrates intersecting each other so as to have an opening that at least one of the apertures faces.

6. The perforated-structure body according to claim 5, wherein the plurality of first support substrates and the plurality of second support substrates orthogonally intersect each other and form a rectangular opening.

7. The perforated-structure body according to claim 4, wherein the first support substrate and the second support substrate intersect each other diagonally.

8. The perforated-structure body according to claim 4, wherein a corner where the first support substrate and the second support substrate intersect each other has a curved shape.

9. The perforated-structure body according to claim 3, wherein the first and second support substrates are alternately arranged on the at least one of the first main surface and the second main surface.

10. The perforated-structure body according to claim 3, wherein the second support substrate surrounds a periphery of the first support substrate.

11. The perforated-structure body according to claim 10, wherein the first support substrate has an annular shape and the second support substrate has an annular shape having a larger inner dimension than the first support substrate.

12. The perforated-structure body according to claim 1, wherein the support substrate has a triangular shape.

13. The perforated-structure body according to claim 3, wherein the first support substrate and the second support substrate each have a triangular shape.

14. A perforated-structure body comprising:
a plate having a first main surface and a second main surface that opposes the first main surface, and a plurality of apertures that penetrate from the first main surface to the second main surface; and
a support substrate that is stacked on at least one of the first main surface and the second main surface of the perforated plate, the support substrate defining a portion through which at least one of the apertures is exposed,
wherein the support substrate has a central portion and first and second end portions that are arranged on either side of the central portion, and a thickness of the first and second end portions is smaller than a thickness of the central portion.

15. The perforated-structure body according to claim 14, wherein a sectional shape of the support substrate in a direction that connects the first and second end portions in a thickness direction of the support member is in an arch shape.

16. A manufacturing method for manufacturing the perforated-structure body according to claim 1, the method comprising:
preparing the plate; and
forming the support substrate on the at least one of the first main surface and the second main surface of the plate so that the first aperture is exposed through the portion of the support substrate and the second aperture is closed by the support substrate.

17. The manufacturing method for manufacturing the perforated-structure body according to claim 16, wherein the support substrate is formed using a plating method and the support substrate is formed such that part of the support substrate is accommodated inside at least one of the apertures covered by the support substrate at the time of plating.

18. A measurement apparatus comprising:
the perforated-structure body according to claim 1;
an electromagnetic wave radiating apparatus that radiates electromagnetic waves onto the perforated-structure body; and
an electromagnetic wave detection unit that measures a characteristic of electromagnetic waves that have been transmitted through the perforated-structure body,
wherein a measurement target is detected based on a change in a characteristic of the electromagnetic waves caused by the measurement target arranged adjacent the first or second main surface of the perforated-structure body.

19. A measurement method comprising:
obtaining a reference value by radiating electromagnetic waves onto the perforated-structure body according to claim 1 and detecting electromagnetic waves that have been transmitted through the perforated-structure body;
arranging a measurement target adjacent the first or second main surface of the perforated-structure body;
radiating electromagnetic waves at the perforated-structure body having the measurement target and then detecting electromagnetic waves that have been transmitted through the perforated-structure body having the measurement target; and
detecting a characteristic of the measurement target based on a difference between the electromagnetic waves transmitted through the perforated-structure body having the measurement target and the reference value of the electromagnetic waves.

\* \* \* \* \*